United States Patent
Litterst et al.

(10) Patent No.: US 9,702,822 B2
(45) Date of Patent: Jul. 11, 2017

(54) DIGITAL ASSAYS WITH A REPORTER FOR AMPLICON LENGTH

(71) Applicant: Bio-Rad Laboratories, Inc., Hercules, CA (US)

(72) Inventors: Claudia Litterst, Walnut Creek, CA (US); Austin P. So, Pleasanton, CA (US); Duc Do, San Jose, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 216 days.

(21) Appl. No.: 13/973,940

(22) Filed: Aug. 22, 2013

(65) Prior Publication Data

US 2014/0057273 A1     Feb. 27, 2014

Related U.S. Application Data

(60) Provisional application No. 61/692,635, filed on Aug. 23, 2012.

(51) Int. Cl.
  *C12Q 1/68*   (2006.01)
  *C12P 19/34*   (2006.01)
  *G01N 21/64*   (2006.01)

(52) U.S. Cl.
  CPC ....... *G01N 21/6486* (2013.01); *C12Q 1/6846* (2013.01); *C12Q 1/6851* (2013.01); *C12Q 1/6858* (2013.01)

(58) Field of Classification Search
  None
  See application file for complete search history.

(56) References Cited

U.S. PATENT DOCUMENTS

2013/0178378 A1*  7/2013  Hatch ............... C12Q 1/686
                                                                506/9

FOREIGN PATENT DOCUMENTS

WO     2011100604 A2     8/2011
WO     2014149480 A1     9/2014

OTHER PUBLICATIONS

Martin et al. (2005) BMC Microbiology vol. 5:38 doi:10.1186/1471-2180-5-28.*
Higuchi et al. (1993) Biotechnology vol. 11 pp. 1026-1030.*
Higuchi et al. (1992) Biot4echnology vol. 10 pp. 413-417.*
Pohl et al. (2004) Expert Rev. Mol. Diagn. 4 (1), 41-47.*
Hindson et al. (2011) Anal. Chem. vol. 83: 8604-8610.*
Ye et al. (2001) Nucl. Acids Res. vol. 29 No. 17 e88.*
Mao et al. (2007) BMC Biotechnology vol. 7: 76 doi:10.1186/1472-6750-7-76.*
Wu et al (2008) Eur. Food Res technol. vol. 227: pp. 1117-1124. DO I 10.1007/s00217-008-0827-9.*

(Continued)

*Primary Examiner* — Young J Kim
(74) *Attorney, Agent, or Firm* — Kolisch Hartwell, P.C.

(57) ABSTRACT

Digital assay system, includes methods, apparatus, and compositions, for distinguishing and measuring different types of templates according to the different lengths of corresponding amplicons, which may be amplified by the same pair of primers. The system may include a length-sensitive reporter generating luminescence that varies according to amplicon length. The system may, for example, be utilized to identify, distinguish, and/or quantify wild-type and mutant/variant templates, processed and unprocessed template, a target template and a primer dimer, or the like.

8 Claims, 10 Drawing Sheets

(56) References Cited

OTHER PUBLICATIONS

Richard M. Cawthon, "Telomere measurement by quantitative PCR", Nucleic Acids Research, Mar. 23, 2002, vol. 30, No. 10, pp. 1-6.
Weijie Wang et al., "DNA quantification using EvaGreen and a real-time PCR instrument", ScienceDirect Analytical Biochemistry Jun. 9, 2006, vol. 356, No. 2, pp. 303-305.
Fei Mao et al., "Characterization of EvaGreen and the implication of its physicochemical properties for qPCR applications", BMC Biotechnology, Nov. 9, 2007, vol. 7, No. 76, pp. 1-16.
Tihomir Todorov et al., "A Unified Rapid PCR Method for Detection of Normal and Expanded Trinucleotide Alleles of CAG Repeats in Huntington Chorea and CGG Repeats in Fragile X Syndrome", Mol. Biotechnology, Mar. 9, 2010, vol. 45, No. 2, pp. 150-154.
Lee W. Young, Authorized Officer, International Searching Authority, U.S. Patent and Trademark Office, "International Search Report" in connection with related PCT Patent Application Serial No. PCT/US2013/056286, dated Dec. 2, 2013, 2 pages.
Lee W. Young, Authorized Officer, International Searching Authority, U.S. Patent and Trademark Office, "Written Opinion of the International Searching Authority" in connection with related PCT Patent Application Serial No. PCT/US2013/056286, dated Dec. 2, 2013, 9 pages.
Hindson, Benjamin J. Hindson et al., "High-Throughput Droplet Digital PCR System for Absolute Quantitation of DNA Copy Number", Analytical Chemistry, vol. 83, Oct. 28, 2011, pp. 8604-8610.
Leber, Thomas, Examiner, European Patent Office, "Extended European Search Report" in connection with related European Application No. 13831166.7, dated Mar. 1, 2016, 10 pages.
McDermott, Geoffrey P. et al., "Multiplexed Target Detection Using Dna-Binding Dye Chemistry in Droplet Digital PCR", Analytical Chemistry, vol. 85, Nov. 3, 2013, pp. 11619-11627.
Zimmermann, Bernhard G. et al., "Digital PCR: a powerful new tool for noninvasive prenatal diagnosis?", Prenatal Diagnosis, vol. 28, Nov. 10, 2008, pp. 1087-1093.

\* cited by examiner

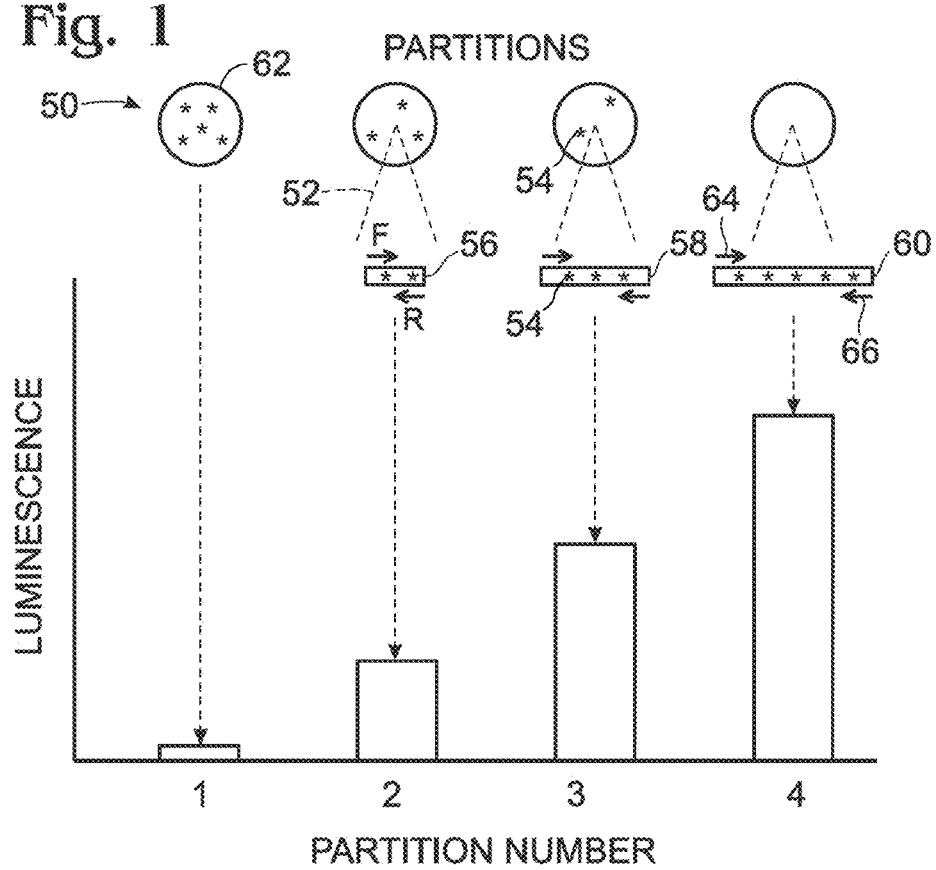

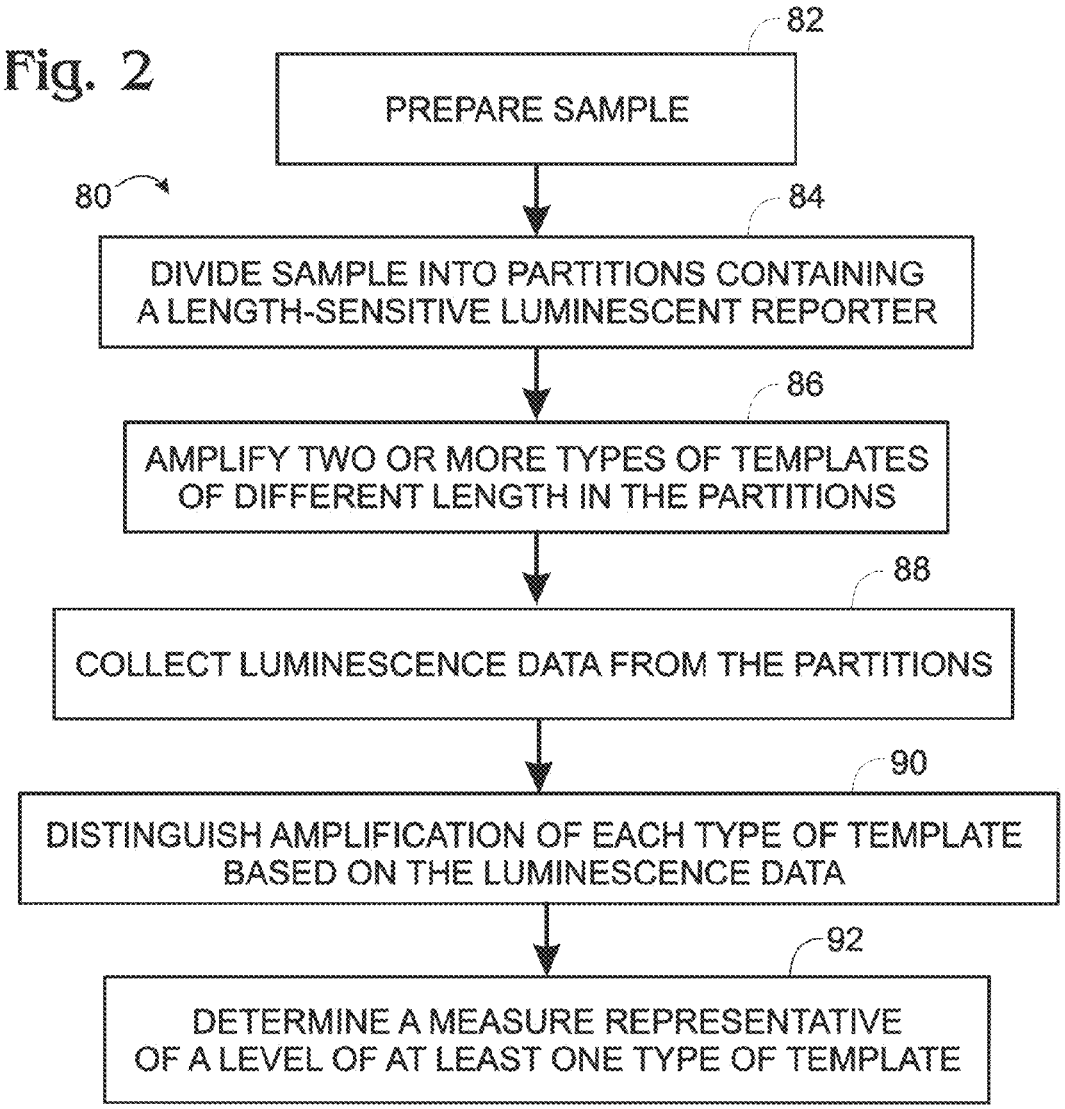
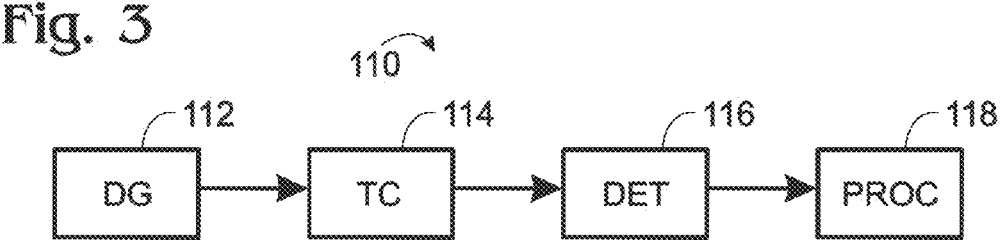

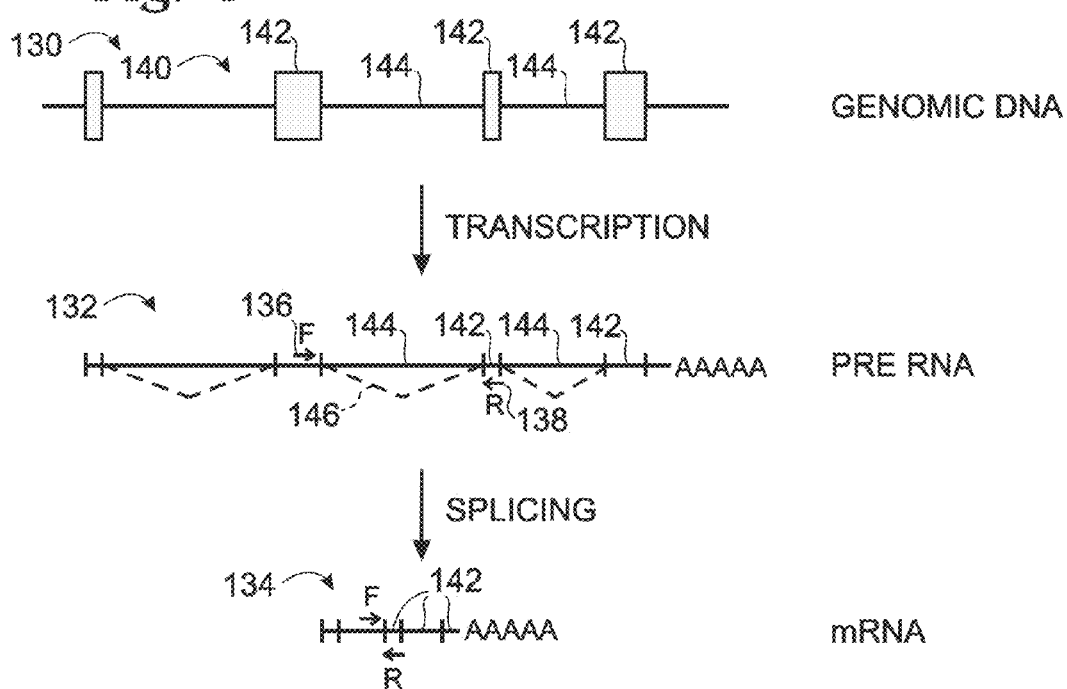
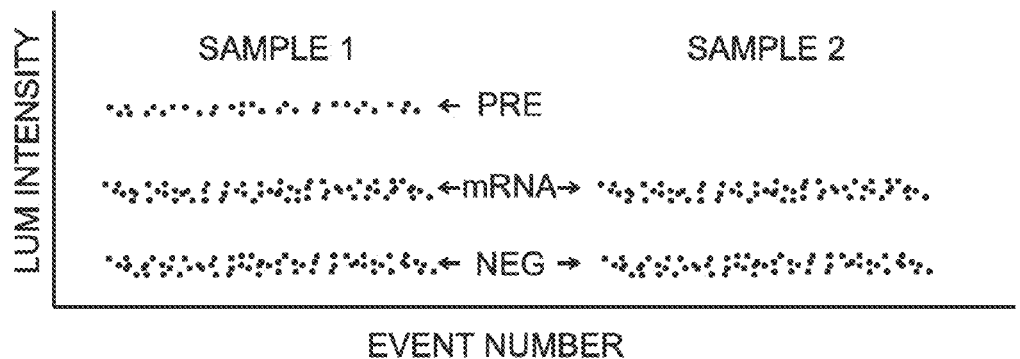

DIGITAL ASSAYS WITH A REPORTER FOR AMPLICON LENGTH

CROSS-REFERENCE TO PRIORITY APPLICATION

This application is based upon and claims the benefit under 35 U.S.C. §119(e) of U.S. Provisional Patent Application Ser. No. 61/692,635, filed Aug. 23, 2012, which is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2013/0040841 A1, published Feb. 14, 2013; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte, such as a nucleic acid template (also termed a target), in a sample. In an exemplary digital assay, a sample is separated into a set of partitions, generally of equal volume, with each containing, on average, about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, may be described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The negative fraction (or, equivalently, the positive fraction) then may be utilized to determine the concentration of the analyte in the partitions by Poisson statistics.

Digital assays frequently rely on amplification of a nucleic acid template in partitions, such as droplets, to enable detection of a single copy of the template. In some cases, amplification may, for example, be conducted via the polymerase chain reaction (PCR), to achieve a digital PCR assay. In any event, amplification of the template to generate a corresponding amplicon in individual partitions can be detected optically by the use of a reporter, such as a sequence-specific probe, included in the reaction. The sequence-specific probe can be labeled with a dye that provides a fluorescence signal indicating whether or not the template has been amplified in each partition.

A digital amplification assay can be multiplexed to permit detection of two or more different templates within each partition. Amplification of the templates can be distinguished by utilizing template-specific probes labeled with different dyes. If a detector for a digital amplification assay can distinguishably measure the fluorescence emitted by N different dyes, then the assay is capable of measuring N different templates. However, instruments with more optical channels, to detect emission from more dyes, are more expensive than those with fewer channels. Also, increasing the number of distinguishable dyes is expensive and becomes impractical beyond a certain number. On the other hand, many applications could benefit from the ability to distinguish amplification of two or more types of template using the same reporter.

SUMMARY

The present disclosure provides a digital assay system, includes methods, apparatus, and compositions, for distinguishing and measuring different types of templates according to the different lengths of corresponding amplicons, which may be amplified by the same pair of primers. The system may include a length-sensitive reporter generating luminescence that varies according to amplicon length. The system may, for example, be utilized to identify, distinguish, and/or quantify wild-type and mutant/variant templates, processed and unprocessed templates, a target template and a primer dimer, or the like.

BRIEF DESCRIPTION OF THE DRAWINGS

FIG. 1 is a graph of exemplary luminescence data that may be collected from partitions containing a length-sensitive reporter and amplified templates (amplicons) of different length, with each partition represented schematically and aligned with a corresponding portion of the luminescence data, in accordance with aspects of the present disclosure.

FIG. 2 is a flowchart of steps that may be performed in an exemplary digital assay of distinct types of templates using a reporter for amplicon length, in accordance with aspects of the present disclosure.

FIG. 3 is a schematic representation of an exemplary system for performing at least a portion of the digital assay of FIG. 2, in accordance with aspects of the present disclosure.

FIG. 4 is a schematic representation of the relationship between genomic DNA, precursor ("PRE") RNA transcribed from the genomic DNA, and messenger RNA ("mRNA") formed by splicing the precursor RNA, with the same exemplary forward ("F") and reverse ("R") primers positioned to form respective amplicons of different length from cDNA forms of the precursor RNA and messenger RNA, in accordance with aspects of the present disclosure.

FIG. 5 is a plot of exemplary luminescence data that may be collected in the digital assay of FIG. 2 performed with the primers of FIG. 4 and two sets of droplets containing a pair of samples representing different ratios of precursor RNA to mRNA, in accordance with aspects of the present disclosure.

DETAILED DESCRIPTION

Figure 6:
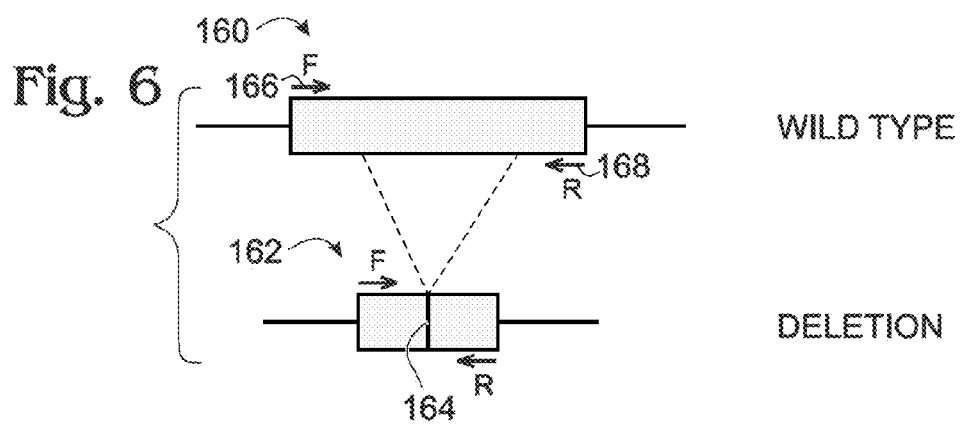
FIG. 6 is a schematic comparison of a pair of templates that may be distinguished in the digital assay of FIG. 2, with the templates being a wild-type template and a shorter mutant (or variant) template representing a deletion of a region of the wild-template, with priming sites for the same pair of forward and reverse primers illustrated for each template, in accordance with aspects of the present disclosure.

The present disclosure provides a digital assay system, includes methods, apparatus, and compositions, for distinguishing and measuring different types of templates according to the different lengths of corresponding amplicons, which may be amplified by the same pair of primers. The system may include a length-sensitive reporter generating luminescence (e.g., photoluminescence, such as fluorescence) that varies according to amplicon length. The system may, for example, be utilized to identify, distinguish, and/or quantify wild-type and mutant/variant templates, processed and unprocessed templates, a target template and a primer dimer, or the like.

A method of performing a digital assay is provided. In the method, at least two types of template (at least two targets) may be amplified in partitions to generate at least two types of amplicons of different length. The partitions may contain a same luminescent length-sensitive reporter that interacts with each type of amplicon, to produce a luminescence characteristic (e.g., photoluminescence intensity, polarization, lifetime, resonance energy transfer, etc.) that varies among the partitions according to the length of amplicon, if any, generated in each partition. Data representing the luminescence characteristic may be collected from the partitions. Amplification of each type of template/target in individual partitions may be distinguished based on the data.

Another method of performing a digital assay is provided. In the method, at least two types of templates/targets may be amplified in droplets of a same emulsion with a same pair of primers to generate at least two types of amplicons of different length. The droplets may contain a same length-sensitive luminescent reporter that interacts with each type of amplicon. The droplets may be illuminated with excitation light to induce light emission from the reporter that varies in intensity among the partitions according to the length of amplicon, if any, generated in each partition. Data representing light emitted by the droplets may be collected. Amplification of each type of template/target in individual droplets may be distinguished based on the data.

The system disclosed herein may have substantial advantages over other digital assays with multiplexed analysis of two or more targets in the same set of partitions, such as droplets of an emulsion. Use of a length-sensitive reporter that binds to each amplified target permits the detection of insertions and deletions based on amplitude differences of the targeted amplicon. Primers may be designed to flank the site of interest containing the insertion or deletion, and run in a digital assay, using an intercalating dye as a fluorescent marker. As fluorescence amplitude is related to amplicon length, an increase or decrease in amplitude relative to the wild-type target indicates an insertion or deletion in that particular locus. This variation in amplitude can be used to detect a very small fraction of mutant species. A relevant example is the detection of deletions or insertions associated with cancer, such as the exon 19 deletion in the EGF receptor. Another example is the detection of precursor mRNA species, where the introns have not been removed completely from the RNA molecule. The presence of an immature RNA versus its mature counterpart would produce droplets having higher fluorescence amplitude.

The digital assays of the present disclosure have numerous advantages over other approaches. For insertion or deletion assays based on other approaches, the length of differences relative to wild type are variable, which can preclude the ability to create a single digital assay that captures most variants. The present disclosure allows the use of conserved primers and differences in fluorescence amplitude produced by length differences to detect variants of different size. Similar results cannot be obtained in real-time PCR assays using intercalating dyes. Also, performing the digital assays of the present disclosure in small volumes, such as droplets, limits competitive effects among different types of targets, including abundant targets and rare mutant targets. Fluorescence in situ hybridization alternatively could be employed, but resolution is poor and the procedure is tedious. In contrast, the digital assays of the present disclosure can be relatively quick and quantitative.

Further aspects of the present disclosure are presented in the following sections: (I) overview of an exemplary digital assay system, (II) RNA processing assays, (III) assays for mutations, (IV) genotyping assays, (V) assays that distinguish a target template from primer dimer, and (VI) examples.

I. OVERVIEW OF AN EXEMPLARY DIGITAL ASSAY SYSTEM

This section provides an overview of a digital assay system that uses a length-sensitive reporter to distinguish amplification of different nucleic acid templates (interchangeably termed targets) in the same set or different sets of partitions; see FIGS. 1-3.

FIG. 1 shows a graph or plot of exemplary luminescence data that may be collected from individual partitions 50 containing, indicated at 52, a length-sensitive reporter 54 ("*") and two or more types of amplified template (e.g., amplicons 56-60 of different length generated by amplification of corresponding templates). Each partition, which may or may not be a droplet 62, is represented schematically and aligned with a corresponding bar of the graph.

The same pair of primers 64, 66 may be used to amplify the different types of templates in the partitions. Each type of template may have a binding site for each primer, with the length of intervening sequence between the primer binding sites being different for the different types of templates, which may be a result of one or more insertions and/or deletions. Primers 64, 66 may be described as a forward primer ("F") and a reverse primer ("R"), to distinguish the primers from one another and indicate the convergent directions in which the primers are extended. Each primer may be an oligonucleotide composed of any suitable number of nucleotides, such as about 10-200, 15-100, or 20-75 nucleotides, among others. In some cases, templates of different length may be amplified by respective distinct combinations of primers.

Reporter 54 may be a luminescent reporter, such as a photoluminescent reporter that emits light in response to excitation with light. Accordingly, the reporter may be fluorescent or phosphorescent, among others. The reporter may be a generic reporter for single-stranded and/or double-stranded nucleic acid that interacts with nucleic acid at least generally nonspecifically, such that the reporter can interact detectably with each type of amplicon, optionally in direct relation to the length of the amplicon. For example, as shown in FIG. 1, more reporter (e.g., more reporter molecules) may interact with a longer amplicon and less reporter (e.g., fewer reporter molecules) with a shorter amplicon, if compared per individual amplicon complex and/or with equal molar amounts of each type of amplicon. Unbound reporter 54 is shown in FIG. 1 as being spaced from each amplicon.

A characteristic of the luminescence of the reporter may be altered substantially by interaction with amplicons. For example, luminescence intensity, luminescence polarization, luminescence resonance energy transfer, and/or luminescence lifetime, among others, of the reporter may substantially increase or decrease in response to amplicon binding. The luminescence characteristic may be a photoluminescence characteristic, such as a fluorescence characteristic, a phosphorescence characteristic, or the like. The magnitude or amplitude of the characteristic may be measured to distinguish the presence of different types of templates in the partitions. For example, in the present illustration, the magnitude of the characteristic is directly related to template length, with a partition containing no template giving the weakest signal (the partition on the far left), and a partition containing the longest template giving the strongest signal (the partition on the far right).

In some cases, the relationship between amplicon length and luminescence may plateau and/or become inverted as amplicon length is increased above a threshold length, such as about 500, 750 or 1000 nucleotides among other. This effect may be caused by a decreased efficiency of template/target amplification with lengths above the threshold. Accordingly, assays may be designed to identify, distinguish, and/or quantify targets that produce amplicons below the threshold length. Also, in some cases, a shorter target may outcompete a longer target for amplification with the same pair of primers in the same partition, such that amplification of only the shorter target is detected in that partition. Accordingly, in some cases, determination of the level of a longer target may include compensation for partitions containing both lengths of target.

The reporter may be a dye that interacts with (e.g., binds) nucleic acid. The dye may be a major groove binder, a minor groove binder, an intercalator, or an external binder, among others. The dye may interact preferentially with double-stranded relative to single-stranded nucleic acid and/or may exhibit a greater change in a luminescent characteristic (e.g., intensity) when interacting with double-stranded relative to single-stranded nucleic acid. Exemplary dyes that may be suitable include luminescent cyanines, phenanthridines, acridines, indoles, imidazoles, and the like, such as DAPI, HOECHST 33258, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others.

FIG. 2 shows a flowchart of an exemplary method 80 of performing a digital assay for distinct types of templates using a reporter for amplicon length. The steps presented for method 80 may be performed in any suitable order and in any suitable combination. Furthermore, the steps may be combined with and/or modified by any other suitable steps, aspects, and/or features of the present disclosure.

Sample Preparation.

A sample may be prepared for the assay, indicated at 82. Preparation of the sample may include any suitable manipulation of the sample, such as collection, dilution, concentration, purification, lyophilization, freezing, extraction, combination with one or more assay reagents, performance of at least one preliminary reaction (e.g., fragmentation, reverse transcription, ligation, or the like) to prepare the sample for one or more reactions in the assay, or any combination thereof, among others. Preparation of the sample may include rendering the sample competent for subsequent performance of one or more reactions, such as one or more enzyme catalyzed reactions and/or binding reactions, e.g., amplification of one or more types of templates in the sample.

In some embodiments, preparation of the sample may include combining the sample with reagents for amplification and for reporting whether or not amplification occurred. Reagents for amplification may include any combination of primers for the templates (e.g., the same pair of primers for two or more types of templates), dNTPs and/or NTPs, at least one enzyme (e.g., a polymerase, a ligase, a reverse transcriptase, or a combination thereof, each of which may or may not be heat-stable), and/or the like. Accordingly, preparation of the sample may render the sample (or partitions thereof) capable of amplification of each of one or more types of template, if present, in the sample (or a partition thereof). Reagents for reporting may include a same reporter for at least two types of template of different length. Accordingly, preparation of the sample for reporting may render the sample capable of reporting, or being analyzed for, whether or not amplification has occurred, for each template, and optionally the extent of any such amplification. The reporter may interact at least generally nonspecifically or specifically with each template (or amplicon generated therefrom). In some cases, the reporter may have a general affinity for nucleic acid (single and/or double-stranded) without substantial sequence specific binding. In some cases, the reporter may be a labeled probe that includes a nucleic acid (e.g., an oligonucleotide) labeled with a luminophore, such as a fluorophore or phosphor, among others.

Sample Partitioning.

The sample may be divided or separated into partitions, indicated at 84. Separation of the sample may involve distributing any suitable portion including up to the entire sample to the partitions. Each partition may be and/or include a fluid volume (and/or a particle) that is isolated from the fluid volumes (and/or particles) of other partitions. The partitions may be isolated from one another by a fluid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

In some embodiments, the sample may contain particles (e.g., beads), which may, for example, be paramagnetic and/or composed of a polymer (e.g., polystyrene). The particles may be pre-attached to any suitable component(s), such as one or more types of primer, template(s), or the like, before sample partitioning. The particles may be disposed in the partitions when the sample is distributed to partitions, optionally with an average of about one particle (or less) per partition.

The partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

The partitions, when formed, may be competent for performance of one or more reactions in the partitions. Alternatively, one or more reagents may be added to the partitions after they are formed to render them competent for reaction. The reagents may be added by any suitable mechanism, such as a fluid dispenser, fusion of droplets, or the like.

The partitions may be formed with any suitable average number of template copies per partition. In some cases, a plurality of the partitions may contain no copies of each of the at least two types of template. In some cases, the partitions may contain an average per partition of less than about ten copies of each type of template when the step of amplifying is initiated. For example, the partitions may contain an average per partition of less than about five, three, or two copies of each type of template when the step of amplifying is initiated. The partitions may contain an average of less than one copy per partition of at least one of the types of template when the step of amplifying is initiated.

The partitions when provided (e.g., when formed) may contain each template and/or each target at "limiting dilution," which means that a plurality of the partitions contain no copies of the template/target, another plurality of the partitions contain a single copy (only one copy) of the template/target, and, optionally, yet another plurality of the partitions (e.g., the rest of the partitions) may contain two or more copies of the template/target. The term "limiting dilution" permits but does not require a literal dilution of the sample/reaction mixture providing the template/target, and is not restricted to the case where there is no more than one copy of the template/target in any partition. Accordingly, partitions containing the template and/or a target at limiting dilution may, for example, contain an average of more than, or less than, about one copy, two copies, or three copies, among others, of the template/target per partition when the partitions are provided or formed. Copies of the template (and/or target) may have a random distribution among the partitions, which may be described as a Poisson distribution.

Template Amplification.

Amplification of two or more types of template/target of different length may be performed in the partitions, indicated at 86. Amplification of each template may occur selectively (and/or substantially) in only a subset of the partitions, such as less than about nine-tenths, three-fourths, one-half, one-fourth, or one-tenth of the partitions, among others. In some examples, the amplification reaction may be a polymerase chain reaction and/or ligase chain reaction. Accordingly, a plurality of amplification reactions for a plurality of distinct types of templates may be performed simultaneously in the partitions.

Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature. In some examples, the conditions may include thermally cycling the partitions to promote a polymerase chain reaction and/or ligase chain reaction. Exemplary isothermal amplification approaches that may be suitable include nucleic acid sequence-based amplification, transcription-mediated amplification, multiple displacement amplification, strand displacement amplification, rolling circle amplification, loop-mediated amplification of DNA, helicase-dependent amplification, and single primer amplification, among others.

Data Collection.

Luminescence data may be collected from partitions, indicated at 88. Data collection may include creating one or more signals representative of light detected from the partitions. The signal may represent an aspect of light, such as the intensity, polarization, and/or lifetime of light emitted from the partitions in response to illumination with excitation light. The signal may be created based on detected light emitted from a length-sensitive reporter in the partitions.

Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

Amplification of Each Type of Template Distinguished.

Amplification of each type of template may be distinguished based on the collected luminescence data, indicated at 90. The reporter may report on the type of template, if any, present in each partition. A signal measured from the reporter in the partitions may be analyzed to determine whether or not a particular template type is present in a given partition. A number of partitions that are positive for each type of template may be determined based on the data. The signal detected from each partition, and the partition itself, may be classified as being positive or negative for each of the template types. Classification may be based on the strength (and/or other suitable aspect) of the signal. If the signal/partition is classified as positive (+), for a given type of template, amplification of the template type is deemed to have occurred and at least one copy of the template type is deemed to have been present in the partition before amplification. In contrast, if the signal/partition is classified as negative (−), for a given template type, amplification of the template type is deemed not to have occurred and no copy of the template type is deemed to be present in the partition (i.e., the template type is deemed to be absent from the partition).

Template Level Determination.

A measure representative of a level of at least one type of template may be determined, indicated at 92. The level of each template type may be determined based on the number of partitions that are amplification-positive for the template type. The calculation may be based on each template type having a Poisson distribution among the partitions. The measure may be a relative level of a template type, such as a ratio of the level of one template type to another template type (e.g., a ratio of mutant to wild-type template). The total number of partitions may be counted or, in some cases, estimated. The partition data further may be used (e.g., directly and/or as concentration data) to estimate copy number (CN) and copy number variation (CNV).

An absolute level (e.g., a concentration) of one or more template types may be determined. A fraction of the total number of partitions that are negative (or, equivalently, positive) for a template type may be calculated. The fraction may be calculated as the number of counted negative (or, equivalently, positive) partitions for the template type divided by the total number of partitions.

The concentration of the template type may be obtained. The concentration may be expressed with respect to the partitions and/or with respect to a sample disposed in the partitions and serving as the source of the template type. The concentration of the template type in the partitions may be calculated from the fraction of positive partitions by assuming that template copies have a Poisson distribution among the partitions. With this assumption, the fraction f(k) of partitions having k copies of the template type is given by the following equation:

$$f(k) = (C^k/k!)\exp(-C)$$

Here, C is the concentration of the template type in the partitions, expressed as the average number of template copies per partition. Simplified Poisson equations may be derived from the more general equation above and used to determine template concentration from the fraction of positive partitions. An exemplary Poisson equation that may be used is as follows:

$$C = -\ln(1-f_p)$$

where $f_p$ is the fraction of partitions positive for the template type (i.e., $f_p = f(1)+f(2)+f(3)+\ldots$), which is a measured estimate of the probability of a partition having at least one copy of the template type. Another exemplary Poisson equation that may be used is as follows:

$$C = -\ln(f_n)$$

where $f_n$ is the fraction of negative droplets (or $1-f_p$), which is a measured estimate of the probability of a droplet having no copies of the template type, and C is the concentration as described above.

In some embodiments, an estimate of the concentration of the template type may be obtained directly from the positive fraction, without use of a Poisson equation. In particular, the positive fraction and the concentration converge as the concentration decreases. For example, with a positive fraction of 0.1, the concentration is determined with the above equation to be about 0.105, a difference of only 5%; with a positive fraction of 0.01, the concentration is determined to be about 0.01005, a ten-fold smaller difference of only 0.5%. However, use of a Poisson equation can provide a more accurate estimate of concentration, particularly with a relatively higher positive fraction, because the equation accounts for the occurrence of multiple template copies per partition.

Further aspects of sample preparation, droplet generation, data collection, and template level determination, among others, that may be suitable for the system of the present disclosure are described in the references listed above in the Cross-References, which are incorporated herein by reference.

FIG. 3 shows an exemplary system 110 for performing any suitable combination of steps of the digital assay of FIG. 2. System 110 may include a partitioning assembly, such as a droplet generator 112 ("DG"), a thermal incubation assembly, such as a thermocycler 114 ("TC"), a detection assembly (a detector) 116 ("DET"), and a data processing assembly (a processor) 118 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets) or signals/data, between the assemblies. Any suitable combination of the assemblies may be operatively connected to one another, and/or one or more of the assemblies may be unconnected to the other assemblies, such that, for example, material/data is transferred manually.

Apparatus 110 may operate as follows. Droplet generator 112 may form droplets disposed in a continuous phase. The droplets may be cycled thermally with thermocycler 114 to promote amplification of targets in the droplets. Signals may be detected from the droplets with detector 116. The signals may be processed by processor 118 to determine numbers of droplets and/or template levels, among others

II. RNA PROCESSING ASSAYS

This section describes use of the digital assay of Section I to distinguish and measure precursor RNA and processed mRNA produced from precursor RNA; see FIGS. 4 and 5.

FIG. 4 shows a schematic flowchart illustrating the relationship between genomic DNA 130, precursor ("PRE") RNA 132 transcribed from genomic DNA 130, and messenger RNA 134 ("mRNA") formed by splicing precursor RNA 132. The same exemplary forward ("F") and reverse ("R") primers 136, 138 are positioned to amplify amplicons of different length from cDNA reverse-transcribed from the precursor RNA and messenger RNA.

The genomic DNA provides an exemplary gene 140 formed of exons 142 separated from one another by introns 144. Transcription of gene 140 produces precursor or heteronuclear RNA 132, which may be a primary transcript containing each of the exon and intron sequences. Splicing of precursor RNA 132, indicated by dashed lines at 146, to remove introns 144, generates messenger RNA 134, which may be translatable to form a polypeptide encoded by the mRNA. The digital assays disclosed herein permit analysis of precursor RNA and mRNA with the same pair of primers, the same reporter, and the same set of partitions, because the amplicon corresponding to precursor RNA may be longer than the amplicon corresponding to mRNA.

FIG. 5 shows a graph of exemplary luminescence data that may be collected in the digital assay of FIG. 2 performed with droplets as partitions. The assay may be performed with the pair of primers of FIG. 4, a length-sensitive reporter, and two sets of droplets each containing a different sample (Sample 1 and Sample 2) representing a different ratio of precursor RNA ("PRE") to mRNA.

The graph plots luminescent intensity as a function of event number (or time). Each event, graphed as a dot, is a change in luminescent intensity (or other luminescence characteristic) representing a detected droplet. In other words, each detected droplet has a corresponding dot/point on the graph. The events may be detected serially with the droplets traveling through a detection site, may be detected in parallel by imaging a field of droplets (e.g., a monolayer of droplets), or the like. In any event, the luminescence characteristic detected for each droplet allows the droplet to be identified as a negative droplet containing no template ("NEG"), a droplet containing the mRNA template ("mRNA"), or a droplet containing the precursor RNA template ("PRE") or other variant template. In the present illustration, Sample 1 contains a detectable level of precursor RNA, but Sample 2, which is kept separate from Sample 1 during droplet generation, amplification, and detection, does not. In other examples, additional RNA variants of additional sizes (i.e., larger or smaller than the mRNA template and/or precursor RNA template) may be distinguished and identified by their distinguishable luminescence characteristics (e.g., distinct droplet intensities). In other examples, droplets from different samples may be intermixed (i.e., interspersed with one another) before amplification or detection if the droplets of different samples are marked distinguishably.

The collected data of FIG. 5 may be used to determine a level of the precursor RNA and/or mRNA in each sample. The level may represent a ratio of template levels, a concentration of one or more templates, or the like.

III. ASSAYS FOR MUTATIONS

This section describes use of the digital assay system of Section I to distinguish and quantify wild-type and mutant templates; see FIGS. 6-10.

FIG. 6 shows a pair of templates 160, 162 of different length that may be distinguished in the digital assay of FIG. 2. Mutant template 162, which also or alternatively may be described as a variant template, may be a shorter derivative of wild-type template 160 resulting from a deletion 164 of one or more nucleotides from the wild-type sequence. Both templates can be amplified with the same pair of forward and reverse primers 166, 168. The templates may be provided by genomic DNA (e.g., by one or more exons and/or introns of a gene), RNA (e.g., via reverse transcription of the RNA to amplifiable cDNA), or the like.

Figure 7:
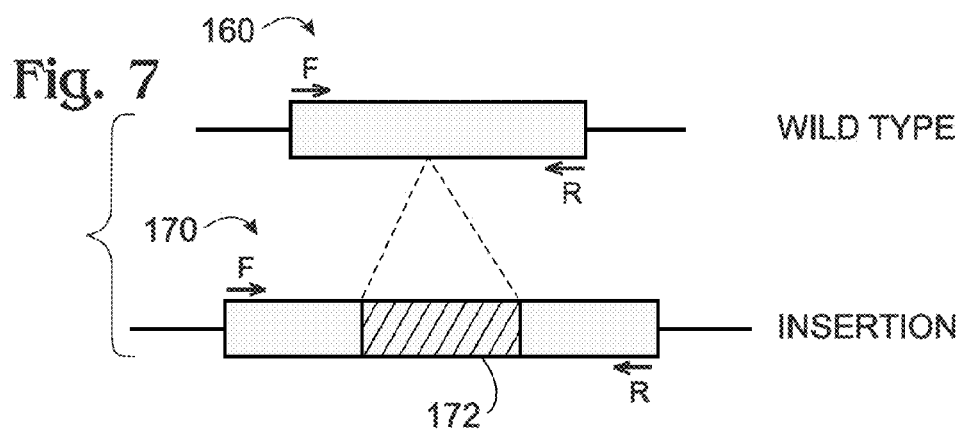
FIG. 7 is a schematic comparison of the wild-type template and primers of FIG. 6 and a longer mutant (or variant) template representing an insertion in the wild-type template, in accordance with aspects of the present disclosure.

FIG. 7 shows another pair of templates 160, 170 of different length that may be distinguished in the digital assay of FIG. 2. Mutant template 170, which also or alternatively may be described as a variant template, may be a longer derivative of wild-type template 160 resulting from an insertion 172 of one or more nucleotides into the wild-type sequence. Both templates can be amplified with the same pair of forward and reverse primers 166, 168 (also see FIG. 6). The templates may be provided by genomic DNA (e.g., by one or more exons and/or introns of a gene), RNA (e.g., via reverse transcription of the RNA to amplifiable cDNA), or the like.

Figure 8:
FIG. 8 is a plot of exemplary luminescence data that may be collected in the digital assay of FIG. 2 performed with the primers of FIGS. 6 and 7 and three sets of droplets each containing a different sample representing a different ratio of the wild-type template and mutant templates of FIGS. 6 and 7, in accordance with aspects of the present disclosure.

FIG. 8 shows a graph plotting exemplary luminescence data that may be collected in the digital assay of FIG. 2 performed with the primers of FIGS. 6 and 7 and three sets of droplets each containing a different sample (Samples 1-3) representing a different ratio of wild-type template 160 ("WT"), deletion template 162 ("DELETION"), and insertion template 170 ("INSERTION"). In particular, Sample 1 contains no detectable insertion or deletion template, Sample 2 contains detectable deletion template but no insertion template, and Sample 3 contains detectable insertion template but no deletion template. In other examples, the samples may contain two or more different types of mutant templates of different length, such as two or more types of deletion template, two or more types of insertion template, or a combination thereof, among others. Accordingly, in some cases, a sample may be assayed to determine a level of mutation, which may, for example, be determined as a relative amount of mutant relative to wild type, an absolute level of all detectable mutants (combined) in the sample, or the like.

Figure 9:
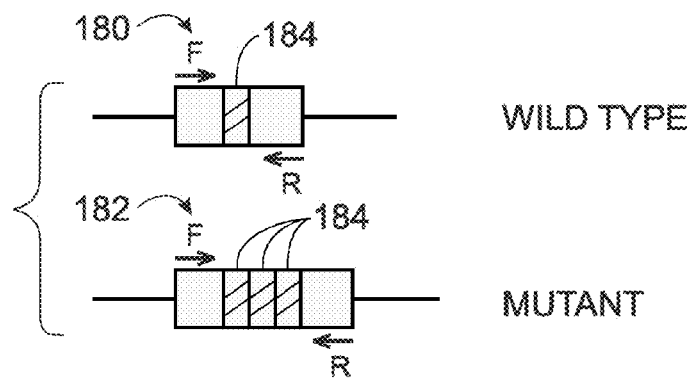
FIG. 9 is a schematic comparison of a pair of templates that may be distinguished in the digital assay of FIG. 2, with the templates being a wild-type template and a mutant template containing a repeated element, in accordance with aspects of the present disclosure.

FIG. 9 shows a pair of templates 180, 182 that may be distinguished in the digital assay of FIG. 2 due to a repeated element 184 that varies in copy number between the templates. In particular, wild-type template 180 contains one copy of the repeated element and mutant template 182 has three copies, which increases the length of the mutant template sufficiently for the corresponding amplicons of the templates to be distinguished by a difference in luminescence. Each of templates 180, 182 can be amplified with the same pair of primers.

Figure 10:
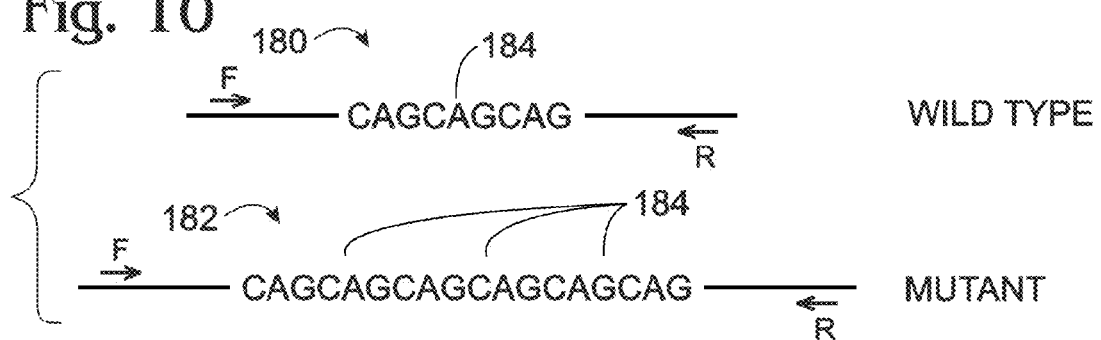
FIG. 10 a schematic comparison according to FIG. 9, where each template has a different number of tandem repeats of the trinucleotide CAG, in accordance with aspects of the present disclosure.

FIG. 10 shows an example of the template configurations of FIG. 9, where each template has a different number of tandem repeats of the trinucleotide CAG. The digital assays disclosed here may determine the number of repetitive elements present in a template. The assay of repetitive elements may be utilized clinically to diagnose and monitor pathologies/conditions that involve repetitive elements, such as Huntington's disease (CAG)n, Spinocerebellar ataxia ((CGG)$_n$ or (CAG)$_n$), and Fragile X, among others. The assay of repetitive elements also may be utilized to characterize telomere length, Alu repeats, and/or LINE1 elements, among others.

IV. GENOTYPING ASSAYS

Figure 11:
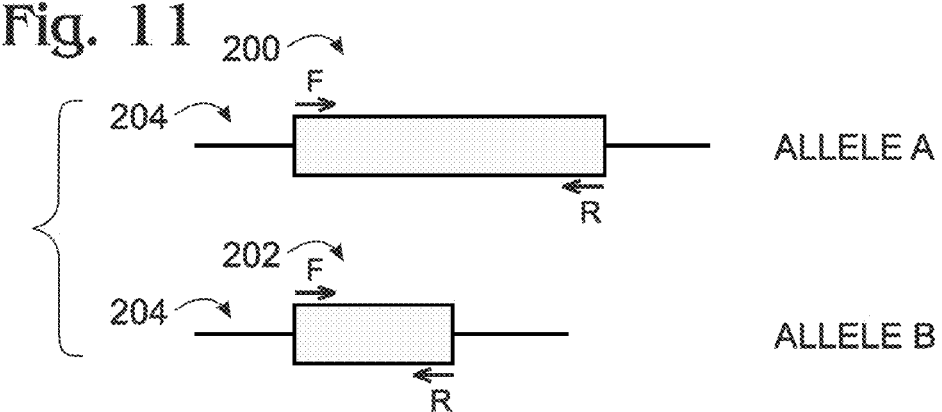
FIG. 11 is a schematic comparison of distinct alleles of the same gene that may be distinguished in the digital assay FIG. 2, with the alleles providing templates of different length for the same pair of forward and reverse primers, in accordance with aspects of the present disclosure.
Figure 12:
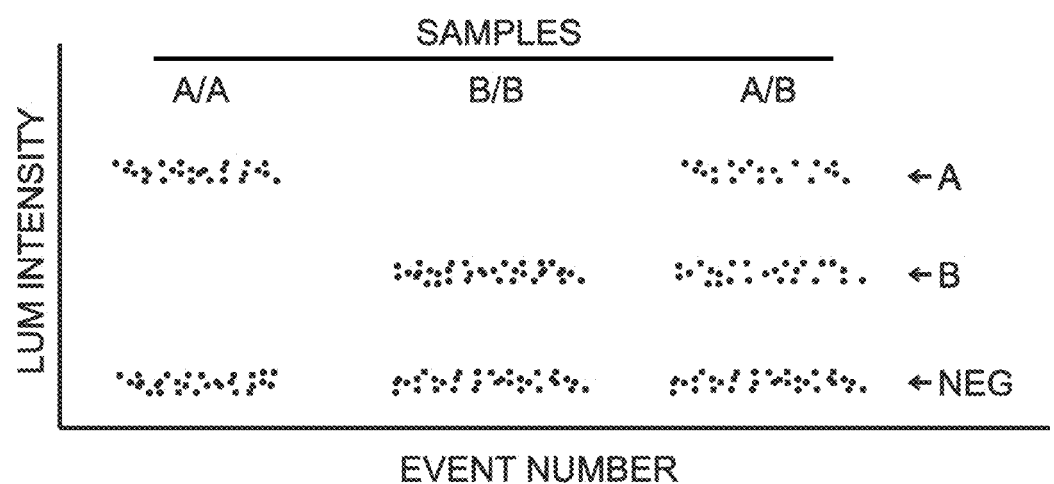
FIG. 12 is a plot of exemplary luminescence data that may be collected in the digital assay of FIG. 2 performed with the primers of FIG. 11 and three sets of droplets each containing a different sample with a distinct combination of the alleles of FIG. 11, in accordance with aspects of the present disclosure.

This section describes use of the digital assay system of Section I to genotype samples; see FIGS. 11 and 12.

FIG. 11 shows a comparison of distinct, established alleles 200, 202 of the same gene or locus 204 that may be distinguished in the digital assay of FIG. 2. The alleles provide templates of different length and amplifiable by the same pair of primers. Each allele may be inherited from a parent via germ line transmission.

FIG. 12 shows a graph plotting exemplary luminescence data that may be collected in the digital assay of FIG. 2 performed with the primers of FIG. 11 and three separate sets of droplets each containing a distinct combination of the alleles of FIG. 11. In particular, the first sample contains only A alleles 200 (e.g., corresponding to an NA diploid genotype), the second sample contains a pair of B alleles 202 (e.g., corresponding to a B/B diploid genotype), and the third sample contains an equal number of A and B alleles 200, 202 (e.g., corresponding to an NB diploid genotype). The assay of FIG. 12 may be performed with genomic DNA, mitochondrial DNA, chloroplast DNA, or cDNA as template, among others. In some cases, the level of one or more of the alleles may be compared with a reference template in the assay (e.g., a template having a known copy number, such as two copies per cell).

V. ASSAYS THAT DISTINGUISH A TARGET TEMPLATE FROM PRIMER DIMER

Figure 13:
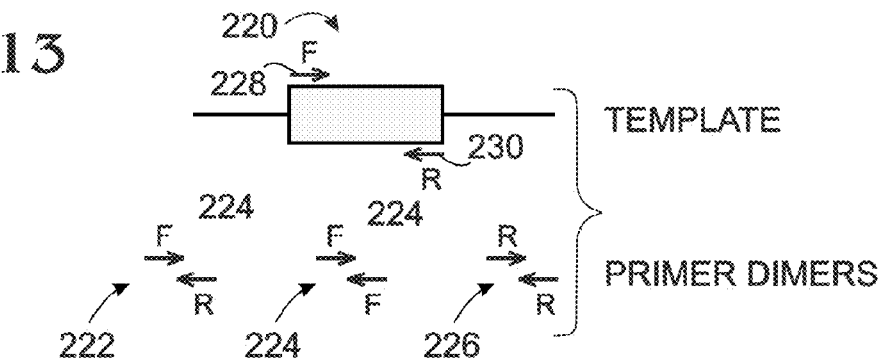
FIG. 13 is a schematic comparison of a target template and various primer dimers that may be distinguished from the target template in the digital assay of FIG. 2, in accordance with aspects of the present disclosure.
Figure 14:
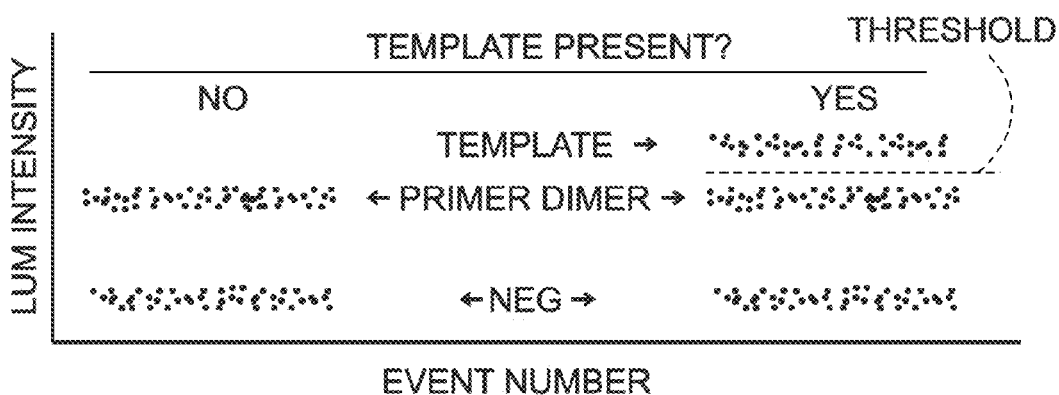
FIG. 14 is a plot of exemplary luminescence data that may be collected in the digital assay of FIG. 2 performed with the primers and target template of FIG. 13, with primer dimers being amplified in only a subset of the droplets lacking the target template, in accordance with aspects of the present disclosure.

This section describes use of the digital assay system of Section I to distinguish amplification of a target template and primer dimers; see FIGS. 13 and 14.

FIG. 13 shows a target template 220 and primer dimers 222-226 that may be distinguished from the target template in the digital assay of FIG. 2. The target template and each of the primer dimers is amplifiable with the same pair of primers 228, 230. Accordingly, one or more of the primer dimers shown can increase background by generating false-positive droplets, particularly with a nonspecific reporter. However, if the target template has a different length than each primer dimer template that is amplified, partitions containing amplified target template can be distinguished from those with amplified primer dimer based on measured luminescence.

FIG. 14 shows a graph plotting exemplary luminescence data that may be collected in the digital assay of FIG. 2 performed in droplets containing the target template and primers of FIG. 13. The luminescence intensity of droplets containing amplified target template is distinguishably higher than for droplets containing amplified primer dimer template (or no detectable amplification (NEG)). Here, primer dimer amplification occurs stochastically, that is, in only a subset of the droplets in the negative control. In other cases, primer dimer amplification may occur in substantially every droplet that lacks the target template. In any event, amplification of the target template may outcompete and/or suppress amplification of primer dimer template in target template-positive droplets. A level of target template may be determined from the number of droplets that are amplification positive for the target template, by excluding primer-dimer positive droplets from the calculation.

Measurement of the intensity level of primer-dimer positive droplets can be used to set a suitable intensity threshold for droplets that are positive for a desired target template. In particular, the signal magnitude produced by primer-dimer positive droplets in a negative control assay can be used to select a threshold above that magnitude, as shown on the right in FIG. 14, to exclude the primer-dimer positive droplets from a calculation of desired target template concentration.

VI. EXAMPLES

This section describes selected aspects and embodiments of the present disclosure related to digital assays with a length-sensitive reporter. These examples are intended for illustration only and should not limit or define the entire scope of the present disclosure.

Example 1. Measurement of RNA Levels

This example describes use of the digital assay of Section I to measure levels unprocessed and processed transcripts in a sample; see FIGS. 15-18.

Figure 15:
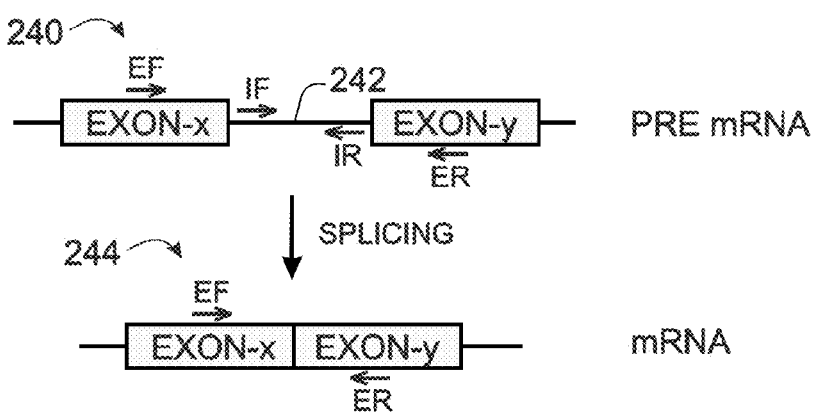
FIG. 15 is a schematic representation of precursor RNA being spliced to form messenger RNA, with the priming positions of exemplary intron and exon primers shown, in accordance with aspects of the present disclosure.

FIG. 15 shows a schematic representation of precursor RNA 240 containing two exons (x and y) separated by an intron 242, and after splicing that removes the intron to form messenger RNA 244. The priming positions of exemplary primers are shown: exon forward ("EF"), intron forward ("IF"), intron reverse ("IR"), and exon reverse ("ER").

Figure 16:
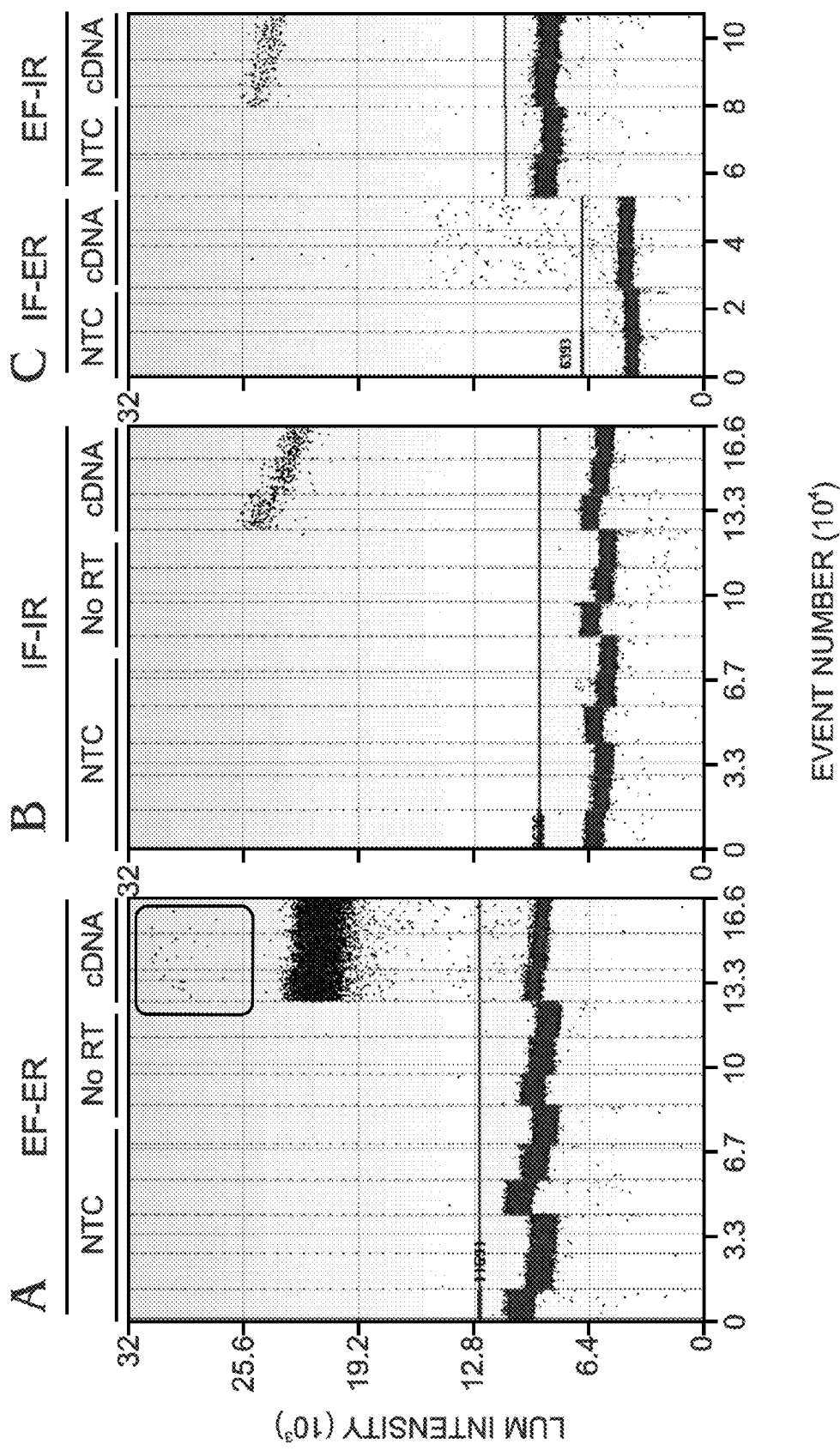
FIG. 16 is a series of plots of luminescence intensity as a function of event number for digital assays performed using various pairs of exon and intron amplification primers for the seventh exon/intron/eighth exon region of glyceraldehyde-3-phosphate dehydrogenase (GAPDH), in accordance with aspects of the present disclosure.

FIG. 16 is a series of plots of luminescence intensity as a function of event number for digital assays performed in droplets on a sample containing glyceraldehyde-3-phosphate dehydrogenase (GAPDH) as template. Various pairs of the exon and intron primers shown in FIG. 15, namely, EF-ER, IF-IR, IF-ER, and EF-IR, were used for amplification of the seventh exon/intron/eighth exon region of GAPDH. "NTC" is a no template (no sample) control. "No RT" indicates the absence of reverse transcriptase and measures amplification from genomic DNA in the sample. "cDNA" measures amplification from cDNA generated by reverse transcription of RNA in the sample. Droplets exhibiting amplification of precursor RNA (from cDNA) with exon primers, which also amplify the processed RNA (from cDNA), are encircled by a rounded box in panel A. The concentration of precursor RNA determined from the luminescence data is about the same for each pair of primers. The lengths of amplicon produced are as follows: EF-ER, 64 bp and 257 bp; IF-IR, 60 bp; IF-ER, 227 bp; and EF-IR, 90 bp.

Figure 17:
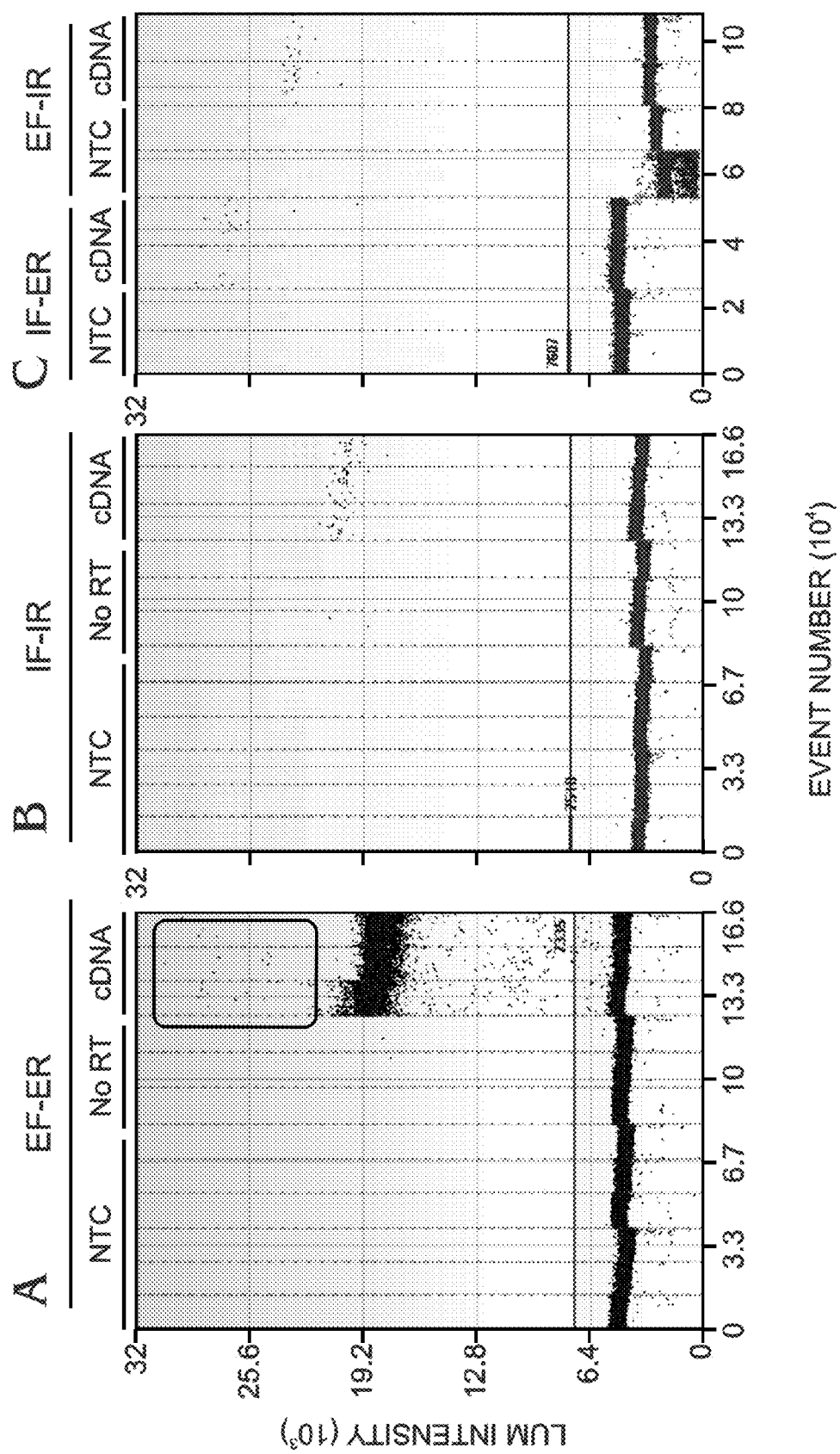
FIG. 17 is a series of plots of luminescence intensity as a function of event number for digital assays performed using various pairs of exon and intron amplification primers for the second exon/intron/third exon region of ribosomal protein large (RPL), in accordance with aspects of the present disclosure.

FIG. 17 shows a series of plots of luminescence intensity as a function of event number for digital assays performed in droplets on a sample containing ribosomal protein large (RPL) as template. Various pairs of the exon and intron primers shown in FIG. 15, namely, EF-ER, IF-IR, IF-ER, and EF-IR, were used for amplification of the second exon/intron/third exon region of RPL. The plots are labeled as in FIG. 16. The lengths of amplicon produced are as follows: EF-ER, 64 bp and 269 bp; IF-IR, 63 bp; IF-ER, 238 bp; and EF-IR, 94 bp.

Figure 18:
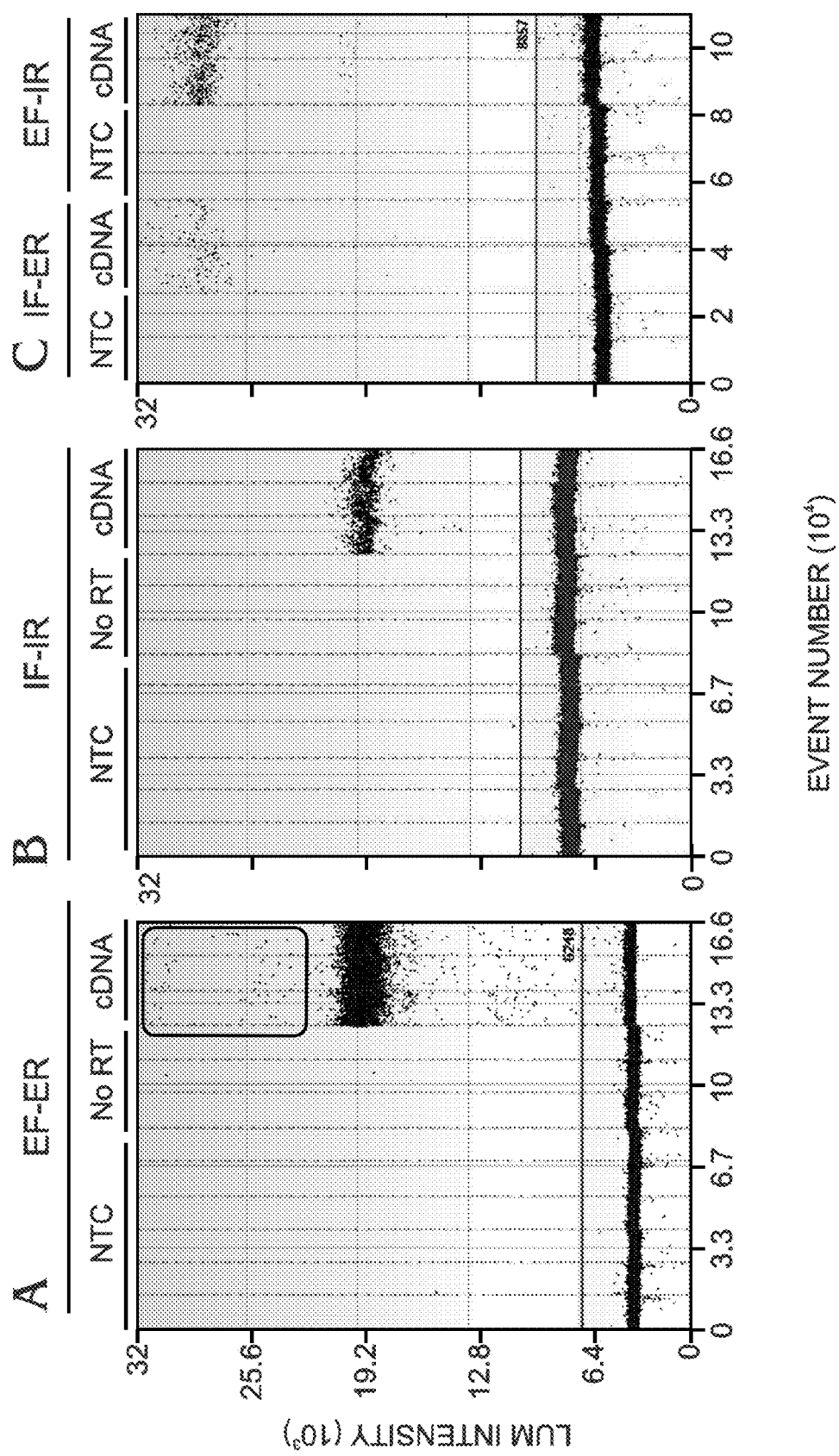
FIG. 18 is a series of plots of luminescence intensity as a function of event number for digital assays performed using various pairs of exon and intron amplification primers for the third exon/intron/fourth exon region of actin, in accordance with aspects of the present disclosure.

FIG. 18 shows a series of plots of luminescence intensity as a function of event number for digital assays performed in droplets on a sample containing actin as template. Various pairs of the exon and intron primers shown in FIG. 15, namely, EF-ER, IF-IR, IF-ER, and EF-IR, were used for amplification of the third exon/intron/fourth exon region of actin. The plots are labeled as in FIG. 16. The lengths of amplicon produced are as follows: EF-ER, 76 bp, 117 bp, and 517 bp; IF-IR, 62 bp; IF-ER, 411 bp; and EF-IR, 67 bp and 168 bp.

Example 2. Selected Embodiments

This example presents selected embodiments of the present disclosure related to digital amplification assays performed with a length-sensitive reporter for amplicons. The selected embodiments are presented as a set of numbered paragraphs.

1. A method of performing a digital assay, comprising: (A) amplifying at least two types of template in partitions to generate at least two types of amplicons of different length, the partitions containing a same luminescent reporter that interacts with each type of amplicon, to produce a luminescence characteristic that varies among the partitions according to the length of amplicon, if any, generated in each partition; (B) collecting data representing the luminescence characteristic from the partitions; and (C) distinguishing amplification of each type of template in individual partitions based on the data.

2. The method of paragraph 1, wherein the at least two types of template include a wild-type template and a mutant template.

3. The method of paragraph 2, wherein the mutant template represents an insertion derivative of the wild-type template.

4. The method of paragraph 2, wherein the mutant template represents a deletion derivative of the wild-type template.

5. The method of any of paragraphs 1 to 4, wherein the at least two types of template include a first template representing at least a portion of a messenger RNA and a second template representing at least a portion of a precursor of the messenger RNA that contains an intron.

6. The method of any of paragraphs 1 to 4, wherein the at least two types of template include a first template and a second template, wherein each of the first template and second template contains the same repeated element of two or more nucleotides, and wherein the repeated element is repeated a different number of times in the first template relative to the second template.

7. The method of paragraph 6, wherein the repeated element is composed of three or more nucleotides.

8. The method of paragraph 7, wherein the repeated element is a trinucleotide.

9. The method of paragraph 6, wherein the repeated element is a telomeric element.

10. The method of any of paragraphs 1 to 9, wherein amplification is performed with the same pair of primers for each template.

11. The method of any of paragraphs 1 to 10, wherein the at least two types of template include a first template provided by a sample being tested and a second template including a primer dimer.

12. The method of any of paragraphs 1 to 11, wherein the luminescent reporter includes an intercalating dye.

13. The method of any of paragraphs 1 to 12, wherein the luminescent reporter binds at least generally nonspecifically to nucleic acid.

14. The method of paragraph 1, wherein the luminescent reporter binds to each amplicon at least generally in direct relation to amplicon length, at least for a range of amplicon lengths.

15. The method of any of paragraphs 1 to 14, wherein the luminescence characteristic is luminescence intensity, wherein the step of collecting data includes a step of detecting of photoluminescence intensity from partitions, and wherein the photoluminescence intensity is optionally fluorescence intensity.

16. The method of any of paragraphs 1 to 15, further comprising a step of illuminating partitions with excitation light that induces light emission from the luminescent reporter, and wherein the step of collecting data includes a step of detecting intensity of the light emission.

17. The method of any of paragraphs 1 to 16, wherein the partitions are droplets.

18. The method of any of paragraphs 1 to 17, wherein a plurality of the partitions contain none of the at least two types of template.

19. The method of any of paragraphs 1 to 18, wherein the partitions contain an average per partition of less than about ten copies of each type of template when the step of amplifying is initiated.

20. The method of any of paragraphs 1 to 19, wherein the partitions contain an average per partition of less than about two copies of at least one of the types of template when the step of amplifying is initiated.

21. The method of any of paragraphs 1 to 20, wherein the partitions contain an average per partition of less than about two copies of each type of template when the step of amplifying is initiated.

22. The method of any of paragraphs 1 to 21, wherein partitions containing the at least two types of template are interspersed with one another when the step of amplifying is initiated.

23. The method of any of paragraphs 1 to 22, wherein the partitions are isolated from one another by walls formed by at least one container.

24. The method of any of paragraphs 1 to 23, further comprising a step of determining a measure representing a level of at least one type of template based on the data.

25. The method of paragraph 24, wherein the measure is a concentration of a template.

26. The method of paragraph 24, wherein the step of determining includes a step of determining a concentration of each type of template.

27. The method of paragraph 24, wherein the measure corresponds to a ratio of template types.

28. The method of any of paragraphs 1 to 27, wherein the at least two types of template include a pair of alleles of a gene.

29. The method of paragraph 28, wherein the steps of amplifying and collecting are performed with a plurality of samples, and wherein the step of distinguishing provides a genotype of each sample with respect to the alleles.

30. A method of performing a digital assay, comprising: (A) amplifying at least two types of template in droplets of a same emulsion with a same pair of primers to generate at least two types of amplicons of different length, the droplets containing a same luminescent reporter that interacts with each type of amplicon; (B) illuminating the droplets with excitation light to induce light emission from the reporter that varies in intensity among the partitions according to the length of amplicon, if any, generated in each partition; (C) collecting data representing the intensity of light emitted by the droplets; and (D) distinguishing amplification of each type of template in individual droplets based on the data.

31. The method of paragraph 30, wherein the step of amplifying includes a step of thermally cycling the droplets.

32. The method of paragraph 31, wherein the step of amplifying is performed by PCR.

33. The method any of paragraphs 30 to 32, wherein the at least two types of template include a wild-type template and a mutant template corresponding to a mutation of the wild-type template.

34. The method of paragraph 33, wherein the mutant template corresponds to an insertion derivative of the wild-type template.

35. The method of paragraph 33, wherein the mutant template corresponds to a deletion derivative of the wild-type template.

36. The method of any of paragraphs 30 to 35, wherein the at least two types of template include a first template representing at least a portion of a messenger RNA and a second template representing at least a portion of a precursor of the messenger RNA that contains an intron.

37. The method of any of paragraphs 30 to 36, wherein the at least two types of template include a first template and a second template, wherein each of the first template and the second template contains the same repeated element of two or more nucleotides, and wherein the repeated element is repeated a different number of times in the first template relative to the second template.

38. The method of paragraph 37, wherein the repeated element is composed of three or more nucleotides.

39. The method of paragraph 38, wherein the repeated element is a trinucleotide.

40. The method of paragraph 37, wherein the repeated element is a telomeric element.

41. The method of any of paragraphs 30 to 40, wherein the at least two types of template include a first template provided by a sample being tested and a second template including a primer dimer.

42. The method of any of paragraphs 30 to 41, wherein a plurality of the droplets contain none of the at least two types of template.

43. The method of any of paragraphs 30 to 42, wherein the droplets contain an average per droplet of less than about ten copies of each type of template when the step of amplifying is initiated.

44. The method of paragraph 43, wherein the droplets contain an average per droplet of less than about two copies of at least one of the types of template when the step of amplifying is initiated.

45. The method of any of paragraphs 30 to 44, wherein the droplets contain an average per droplet of less than about two copies of each type of template when the step of amplifying is initiated.

46. The method of any of paragraphs 30 to 45, further comprising a step of determining a measure representing a level of at least one type of template based on the data.

47. The method of paragraph 46, wherein the measure is a concentration of a template.

48. The method of paragraph 46, wherein the step of determining includes a step of determining a concentration of each type of template.

49. The method of paragraph 46, wherein the measure corresponds to a ratio of template types.

50. The method of any of paragraphs 30 to 49, wherein the at least two types of template include a pair of alleles of a gene.

51. The method of paragraph 50, wherein the steps of amplifying and collecting are performed with a plurality of samples, and wherein the step of distinguishing provides a genotype of each sample with respect to the alleles.

52. A method of performing a digital assay, comprising: (A) amplifying nucleic acid in partitions to generate a first amplicon and a second amplicon of different length and each bound by a same reporter in the partitions; (B) collecting data from the partitions representing light emitted by the reporter, wherein partitions containing the first amplicon are distinguishable in the data from partitions containing the second amplicon based on the light emitted by the reporter; and (C) determining a level of a template for the first amplicon based on the data.

53. The method of paragraph 52, wherein the level is a level of the template present in the partitions before the step of amplifying.

54. The method of paragraph 52, wherein the level is a concentration.

55. A method of performing a digital assay, comprising: (A) generating a first amplicon and a second amplicon in partitions containing a same reporter that binds to each amplicon; (B) collecting data representing light from the reporter in the partitions; and (C) distinguishing a presence of the first amplicon from a presence of the second amplicon in individual partitions based on the data.

56. The method of paragraph 55, wherein the first amplicon represents a target of interest and the second amplicon is an amplification by-product (e.g., template independent).

57. The method of paragraph 56, wherein the amplification by-product is a primer dimer.

58. The method of any of paragraphs 55 to 57, wherein the step of distinguishing is based on a photoluminescence amplitude detected from individual partitions.

59. The method of paragraph 58, wherein partitions are identified as positive for the first amplicon if the photoluminescence amplitude is above a threshold value.

60. The method of any of paragraphs 55 to 59, wherein the step of collecting data is performed with the partitions below a melting temperature of the first amplicon and the second amplicon.

61. The method of paragraph 60, wherein the step of collecting data is performed with the partitions below a temperature of about 45, 40, 35, or 30 degrees Celsius.

62. The method of any of paragraphs 55 to 61, wherein the reporter includes an intercalating dye.

63. The method of any of paragraphs 55 to 62, wherein the partitions are droplets.

64. The method of any of paragraphs 55 to 63, further comprising a step of determining a level of a target corresponding to the first amplicon based on the data.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing a digital assay, the method comprising:
partitioning a same reaction mixture into a plurality of droplets, the reaction mixture containing a first template for a first amplicon, a second template for a second amplicon, two or more primers to generate the first and second amplicons from their corresponding templates, and an intercalating dye, wherein only a subset of the droplets contain a copy of the first template and only a subset of the droplets contain a copy of the second template;

amplifying nucleic acid in the droplets to generate the first amplicon from the first template and the second amplicon from the second template, wherein the first amplicon and the second amplicon are of different length from one another;

detecting an intensity of light emitted by the intercalating dye from individual droplets while the intercalating dye remains bound to the first amplicon and the second amplicon; and comparing the intensity of light detected from each individual droplet to one or more threshold values to classify each individual droplet as negative for both amplicons, positive only for the first amplicon, or positive for the second amplicon.

2. The method of claim 1, wherein the first amplicon and the second amplicon represent distinct first and second alleles of a same gene.

3. The method of claim 1, wherein the first amplicon represents at least a portion of a messenger RNA and the second amplicon represents at least a portion of a precursor of the messenger RNA that contains an intron.

4. The method of claim 1, wherein each of the first amplicon and the second amplicon contains the same repeated element of two or more nucleotides, and wherein the repeated element is repeated a different number of times in the first amplicon relative to the second amplicon.

5. The method of claim 1, wherein the step of amplifying nucleic acid is performed with a same pair of primers to generate the first amplicon and the second amplicon.

6. The method of claim 1, further comprising (i) a step of determining a number of partitions positive or negative for the second amplicon and (ii) a step of determining a level of the second template based on the number of partitions, wherein each of steps (i) and (ii) is performed with a processor.

7. The method of claim 6, wherein the step of determining a level includes a step of calculating a concentration of the second template based on the number using the processor.

8. The method of claim 6, further comprising a step of determining a ratio of the first template to the second template using the processor.

\* \* \* \* \*